(12) United States Patent
Dandiker et al.

(10) Patent No.: US 10,555,592 B2
(45) Date of Patent: Feb. 11, 2020

(54) APPLICATION FOR TOPICAL COMPOSITION

(71) Applicants: Yogesh Dandiker, Edina, MN (US); Paxton Wong, Edina, MN (US)

(72) Inventors: Yogesh Dandiker, Edina, MN (US); Paxton Wong, Edina, MN (US)

(73) Assignee: SYMBIOTEC PHARMA LAB PVT. LTD. (IN)

( * ) Notice: Subject to any disclaimer, the term of this patent is extended or adjusted under 35 U.S.C. 154(b) by 23 days.

(21) Appl. No.: 15/693,398

(22) Filed: Aug. 31, 2017

(65) Prior Publication Data

US 2019/0059552 A1     Feb. 28, 2019

(51) Int. Cl.
  *A61M 35/00*   (2006.01)
  *A45D 34/04*   (2006.01)

(52) U.S. Cl.
  CPC ......... *A45D 34/041* (2013.01); *A61M 35/003* (2013.01); *A45D 2200/054* (2013.01)

(58) Field of Classification Search
  CPC ............ A45D 34/041; A45D 2200/054; A45D 34/00; A45D 34/045; A45D 40/265; A45D 40/28; A45D 2040/00; A45D 2200/20; A61M 35/003; A61M 35/006; A61M 35/00; B05C 17/00; B05C 17/002; B05C 17/005; B05C 17/00503; B05C 17/00506; B05C 17/00516; B05C 17/00569
  See application file for complete search history.

(56) References Cited

U.S. PATENT DOCUMENTS

| | | |
|---|---|---|
| 1,517,914 A | 12/1924 | Macdonald |
| 1,594,636 A | 8/1926 | Smith |
| 1,632,686 A | 6/1927 | Withycombe |
| 1,890,599 A | 12/1932 | Cobello |
| 1,927,462 A | 9/1933 | Marsh-Hunn |
| 1,969,905 A | 8/1934 | Segal |
| 2,187,560 A | 1/1940 | Reilly |
| 2,361,407 A | 10/1944 | McNair |
| 2,526,190 A | 10/1950 | Alvarez |
| 2,532,429 A | 12/1950 | Sparkman |
| 2,818,856 A | 1/1958 | Kohl |

(Continued)

FOREIGN PATENT DOCUMENTS

| EP | 1086904 | 3/2001 |
|---|---|---|
| WO | WO 2003/080463 | 10/2003 |

(Continued)

OTHER PUBLICATIONS

Bandage, Conforming. "New Product Gallery." Nursing Management 18.0 (1987): 4.

(Continued)

*Primary Examiner* — David J Walczak
(74) *Attorney, Agent, or Firm* — Sheppard, Mullin, Richter & Hampton LLP

(57) ABSTRACT

A topical applicator for administration of a composition to a target area. The topical applicator having an applying portion with a cavity defined by at least one side wall, a dividing portion that may be adaptable in shape and/or at least partially permeable, such that it allows a composition to move through it to the cavity, and a target-area contacting portion adapted to create a seal between the cavity and the target area to which the composition is being applied.

16 Claims, 17 Drawing Sheets

(56) References Cited

U.S. PATENT DOCUMENTS

| | | |
|---|---|---|
| 2,853,728 A | 9/1958 | Nadai |
| 2,964,770 A | 12/1960 | Lerner et al. |
| 3,081,769 A | 3/1963 | Ackerman |
| 3,087,189 A * | 4/1963 | Eugene .................. A63B 47/04 401/11 |
| 3,121,905 A | 2/1964 | Shapiro |
| 3,133,308 A | 5/1964 | Claypool |
| 3,133,309 A | 5/1964 | Miles |
| 3,256,551 A | 6/1966 | Schwartzman |
| 3,333,292 A * | 8/1967 | Chase .................... A47L 23/05 15/209.1 |
| 3,456,650 A | 7/1969 | Schwartzman |
| 3,456,851 A | 7/1969 | Mattes et al. |
| 3,486,504 A | 12/1969 | Austin |
| 4,177,811 A | 12/1979 | Alvarez |
| 4,201,491 A | 5/1980 | Kohler |
| 4,483,636 A | 11/1984 | Meyer |
| 4,485,807 A | 12/1984 | Gueret |
| 4,701,167 A | 10/1987 | Chekan |
| 5,019,033 A | 5/1991 | Geria |
| 5,147,337 A | 9/1992 | Plone |
| 5,568,669 A * | 10/1996 | Godown ................ A45D 34/04 132/320 |
| 5,568,990 A | 10/1996 | McAuley |
| 5,615,962 A | 4/1997 | Staub |
| 5,934,296 A | 8/1999 | Clay |
| 6,033,389 A | 3/2000 | Cornish |
| 6,113,008 A | 9/2000 | Arsenault et al. |
| 6,190,367 B1 | 2/2001 | Hall |
| 6,309,128 B1 | 10/2001 | Griebel et al. |
| 6,536,977 B1 | 3/2003 | Hammel |
| 6,688,795 B1 | 2/2004 | Jacob et al. |
| 6,715,951 B2 | 4/2004 | Gueret |
| 7,416,357 B2 | 8/2008 | Thiebaut |
| 7,841,793 B2 | 11/2010 | Ramet |
| 7,845,874 B2 | 12/2010 | Crosnier et al. |
| 7,927,034 B2 * | 4/2011 | Staniforth ............ A61M 35/003 401/262 |
| 8,118,789 B2 | 2/2012 | Abbott et al. |
| 8,157,464 B2 | 4/2012 | Prax |
| 8,177,449 B2 * | 5/2012 | Bayly .................... A45D 34/04 401/11 |
| 8,337,473 B2 | 12/2012 | Zino Gutierrez |
| 8,342,764 B2 | 1/2013 | Bonneyrat |
| 8,419,307 B2 | 4/2013 | Bayly et al. |
| 8,474,505 B2 | 7/2013 | Ozuna et al. |
| 8,807,861 B2 | 8/2014 | Bayly et al. |
| 9,227,044 B2 * | 1/2016 | Bansal ................ A61M 35/003 |
| 9,408,633 B2 | 8/2016 | Leitch |
| 9,615,646 B2 | 4/2017 | Geva et al. |
| 2001/0037095 A1 | 11/2001 | Rucinski |
| 2004/0071494 A1 | 4/2004 | Staniforth et al. |
| 2005/0147459 A1 | 7/2005 | Gerbron |
| 2006/0099026 A1 | 5/2006 | Griffon |
| 2007/0186951 A1 | 8/2007 | Gueret |
| 2010/0217176 A1 | 8/2010 | Carrara et al. |

FOREIGN PATENT DOCUMENTS

| | | |
|---|---|---|
| WO | WO 2015/015384 | 2/2015 |
| WO | WO 2015/040348 | 3/2015 |
| WO | WO 2015/140754 | 9/2015 |
| WO | WO 2016/076406 | 5/2016 |

OTHER PUBLICATIONS

Bryson, Charles Lee, ed. "Health and How to Get it," Hamilton Beach Mfg. Co., 1912, Table of Contents, 1-33.

Cook, David W., "Administration devices and techniques." Drugs and the Pharmaceutical Sciences 88 (1998): 305-356.

Dillingh, Jan et al., "Containers," Practical Pharmaceutics. Springer International Publishing, 2015. 501-536.

Hellbardt, Stefan, and Degenhard Marx. "Trends in skinmedication dispensing." Drug Dev Deliv 13 (2013): 40-45.

Taglietti, M., C. N. Hawkins, and J. Rao. "Novel topical drug delivery systems and their potential use in acne vulgaris." SkinTherapy Lett 13.5 (2008), https://www.skintherapylettercom/acne/novel-topical-drug-delivery-systems/.

* cited by examiner

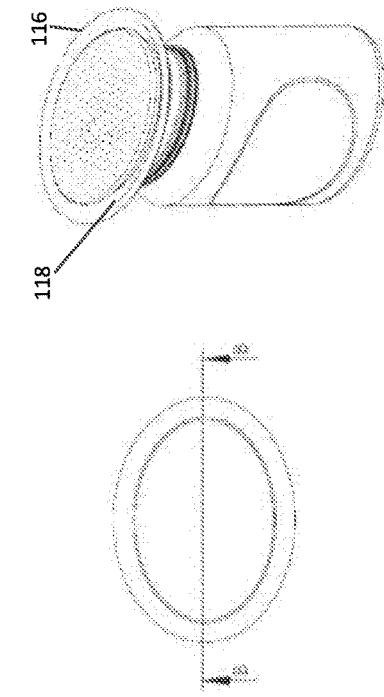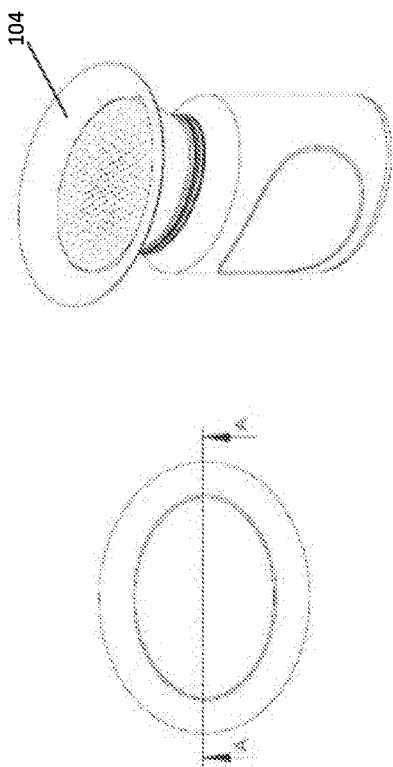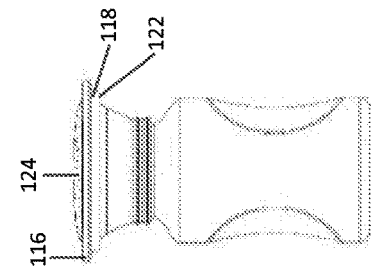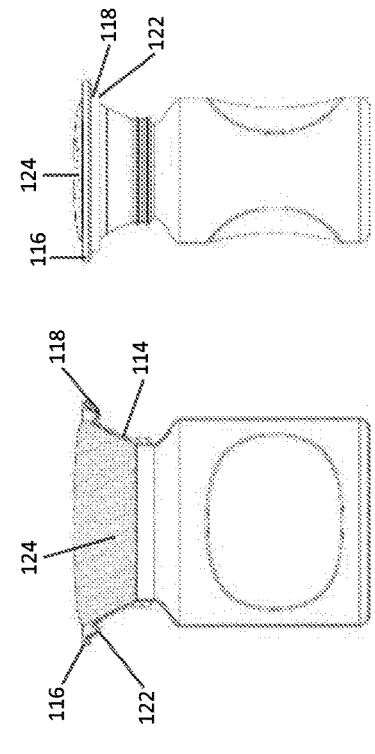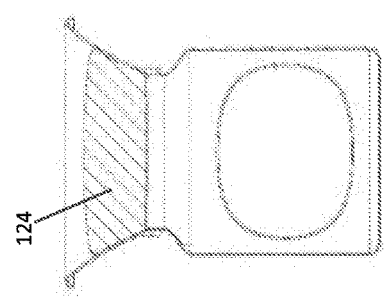

APPLICATION FOR TOPICAL COMPOSITION

CROSS REFERENCE

The present application claims priority under 35 U.S.C. 119(e) to U.S. Provisional 62/348,300, filed on Jun. 10, 2016, which is incorporated by reference herein.

TECHNICAL FIELD

The present disclosure relates generally to an apparatus for applying a treatment to a treatment surface. More particularly, some embodiments of the present disclosure relate to a topical or transdermal composition applicator configured to apply a composition with a degree of precision, thereby inhibiting non-prescribed exposure.

BACKGROUND

Topical medicament compositions, such as liquids, include sunscreens and medicated liquids. They have previously been provided in squeezable containers or in containers with a finger-operated pump, whereby a portion of the composition is deposited on the treatment surface or on a free hand for subsequent application to the treatment surface. In either case, the composition is spread over the treatment surface, such as with a free hand, which results in it being applied to a surface other than the target area.

For some example applications, it is not acceptable for the free hand to be exposed to a medicated composition, such as a liquid, as the medication may be absorbed through the skin on the hand. Some pharmaceutical medications applied to the skin, for example, may have undesirable effects to the user, patient, or others exposed to the medication, if, for example, the medication is applied to areas other than the target area. This is particularly the case where the composition is a topical or transdermal liquid composition intended to have a therapeutic effect at a prescribed dose.

One example of such a composition is testosterone. Transdermal testosterone liquid compositions function as physiologically active agents. Testosterone is used in many forms to treat a wide variety of conditions. In particular, testosterone plays a key role in the development of male reproductive tissues such as the testis and prostate as well as promoting secondary sexual characteristics such as increased muscle, bone mass, and the growth of body hair. In addition, testosterone is essential for health and well-being as well as the prevention of osteoporosis.

For topical or transdermal medicinal compositions, liquid testosterone solutions included, it is often desirable to provide an applicator which temporarily retains the medicinal composition while it is being applied to a specific treatment surface for absorption through the skin of the user. Often, the treatment surface is located in or around the armpit, or axilla region of the user.

Ideally, applicators for topical compositions would create a balance between adequately retaining the composition, while enabling its release onto the treatment surface. Unfortunately, conventional applicators commonly suffer from the inability to release or apply the composition to the treatment area with adequate precision. For example, patients have been known to spill or spread liquid testosterone solution onto other body parts or objects that other people may touch, thereby undesirably receiving a dose of a medicinal composition. In the case of liquid medicinal compositions, solution often runs down the side of a patient's torso when applied to the armpit. This can lead to a non-prescribed exposure to the medication and related undesirable side effects to patients and non-patients alike. In the example case of testosterone, this risk is especially present to non-patient women and children who come into contact with a male patient.

SUMMARY OF THE DISCLOSURE

Some embodiments of the present disclosure are configured to apply a composition to a target area of a user with a degree of precision that inhibits or substantially limits or prevents overflow, spillage, or dripping onto other areas in the process. In some embodiments, the composition is a medicament. In some embodiments, the composition is a medication. In other embodiments, the composition is not a medicament or medication, but rather, for example, a composition meant to merely cover the skin, such as some sun blocks, lotions, perfumes, decorative inks, pigments, and dyes. In some embodiments, the composition takes a solution, liquid, fluid, free-flowing fluid, gel, cream, foam, or viscous solution form. In some embodiments, the composition takes a combination of these and/or other forms.

Application of the composition may be effected, for example, through a combination of structural features of the applicator. Some embodiments provide a resilient applicator with at least one zone configured to promote continuous contact between a target-area contacting portion of the applicator and the target area of the user during application of a medicinal composition. In some embodiments, the contact zone can adapt in shape to the target area in a controlled manner, such as by being fully or partially collapsible or compressible. In other embodiments, the contact zone is circumferential. In still other embodiments, the zone can adapt in shape to the target area in a controlled manner and is circumferential.

In some embodiments, the topical applicator has one or more applying portions. In some embodiments, an applying portion is fully or partially made of silicone rubber. In some embodiments, the applying portion includes a porous surface. In some embodiments, an applying portion includes a sponge, matrix, trough, reservoir, and/or other spatial and/or material configuration capable of receiving and retaining a composition in one or more volumes or amounts, which may include, for example, one or more interstices, grooves, nodes, impressions, and/or indentations. In some embodiments, an applying portion is configured to be disposed in or proximate to a hold portion. In some embodiments, an applying portion can be configured to directly couple to an upper end of a composition holder configured to store, receive, and/or provide doses of a composition to the applying portion. In some embodiments, an applying portion can be configured to couple to an upper end of a hold portion that is configured to couple to a composition holder. In some embodiments, an applying portion has a resilient, circumferential side wall. In some embodiments, an applying portion has a resilient and fully or partially collapsible or compressible side wall. In some embodiments, an applying portion terminates at one end with a target-area contacting portion. In some embodiments, an applying portion is made up of one or more additional portions, which may include a cavity portion and neck portion. In some embodiments, a cavity portion and a neck portion are divided by a divider portion. In some embodiments, a divider portion is porous. In some embodiments, a divider portion can rotate such that it is either porous or non-porous, depending on its configuration. In some embodiments, a divider portion is a closable passage. In some embodiments, a divider portion is a one-way valve. In other embodiments, a divider portion is solid. In some embodiments, a divider portion is fully, partially, or substantially textured. In other embodiments, a divider portion is fully, partially, or substantially smooth.

In some embodiments, a target-area contacting portion can be integral with an applying portion. In some embodiments, a target-area contacting portion can be coupled adjacent to an applying portion. In some embodiments, a target-area contacting portion can be one or more continuous or intermittent surfaces. In some embodiments, a target-area contacting portion is a lip, ridge, shelf, runner, sleeve, or edge. In some embodiments, an applying portion and/or target-area contacting portion includes a wall and/or floor. In some embodiments, an applying portion and/or target-area contacting portion includes a wall and/or floor with at least one controlled-adaptation zone configured to promote contact with a target area of a user during application of a composition. In some embodiments, a wall and/or floor is configured to promote continuous, sealed contact of an applying portion and/or target-area contacting portion with the target area of the user during application of a topical composition. In some embodiments, a wall and/or floor is configured to promote continuous, sealed contact of an applying portion and/or target-area contacting portion with the target area of the user during application of a topical composition by utilizing a fully or partially collapsible or compressible structure.

In some embodiments, the topical applicator includes a hold portion configured to be held by a user. In some embodiments, the hold portion that may constitute a volume configured to store a composition that is not being applied when the topical applicator is in use. In some embodiments, a hold portion is detachable and reattachable. In some embodiments, a hold portion is a pump head, a valve, a nozzle, or a combination of one or more of a pump head, a valve, and a nozzle. In some embodiments, a hold portion and composition holder are integral with one another. In some embodiments, a hold portion and composition holder are separate components that may or may not be configured to be connected or coupled to one another, either temporarily or permanently. In some embodiments, a hold portion or composition holder portion releases some of the composition when the topical applicator is in use while retaining some of the composition for subsequent use. In some embodiments, a hold portion or composition holder is provided for single use. In some embodiments, a hold portion or composition holder extends from a lower end to an upper end and has an enclosing side wall adapted to be manipulated or used by hand. In other embodiments, a hold portion or composition holder is adapted to be manipulated through user interaction with an assisting apparatus, such as a grip, cartridge, container, sleeve, insulator, shaft, or button. In some embodiments, a flexible wall and/or floor is disposed about the hold portion or composition holder. In some embodiments, a flexible wall and/or floor extends a distance inward or outward from a longitudinal axis of a hold portion or composition holder. In some embodiments, a flexible wall and/or floor is disposed entirely about all or part of a hold portion or composition holder. In some embodiments, a hold portion or composition holder has an outer side wall which includes a gripping surface configured to enable or assist a user's manipulation and use of the topical applicator. In some embodiments, a gripping sleeve can be placed around an outer wall of a hold portion or composition holder to improve or customize the user's ability to hold and manipulate the topical applicator.

The summary above and more detailed descriptions below are not intended to limit the claimed invention to one or more of the identified embodiments or to identify every possible implementation of the present disclosure. However, the figures and the detailed description that follow more particularly exemplify some embodiments for example and illustrative purposes. Moreover, although the disclosure sometimes describes the topical applicator as a delivery mechanism for testosterone and/or a liquid medicament, those applications are used as examples, and are not intended to limit the scope of the disclosure or claims. For example, other compositions to be applied may be, or include, another hormone, such as estrogen or a progestin, a tanning agent, a moisturizing agent, or a sunscreen. Further compositions may be a solution, liquid, fluid, free-flowing fluid, gel, cream, foam, viscous solution, or a mixture or combination of these and/or one or more other compositions. Additional compositions may include testosterone as an active ingredient, and ethanol, isopropyl alcohol, octisalate, and povidone as inactive ingredients.

BRIEF DESCRIPTION OF THE DRAWINGS

The disclosure can be more completely understood in consideration of the following detailed description of various embodiments of the disclosure, in connection with the accompanying drawings, in which:

FIGS. 3A-3J depict a further embodiment of the disclosure including a hold portion and an applying portion.

Figure 1A:
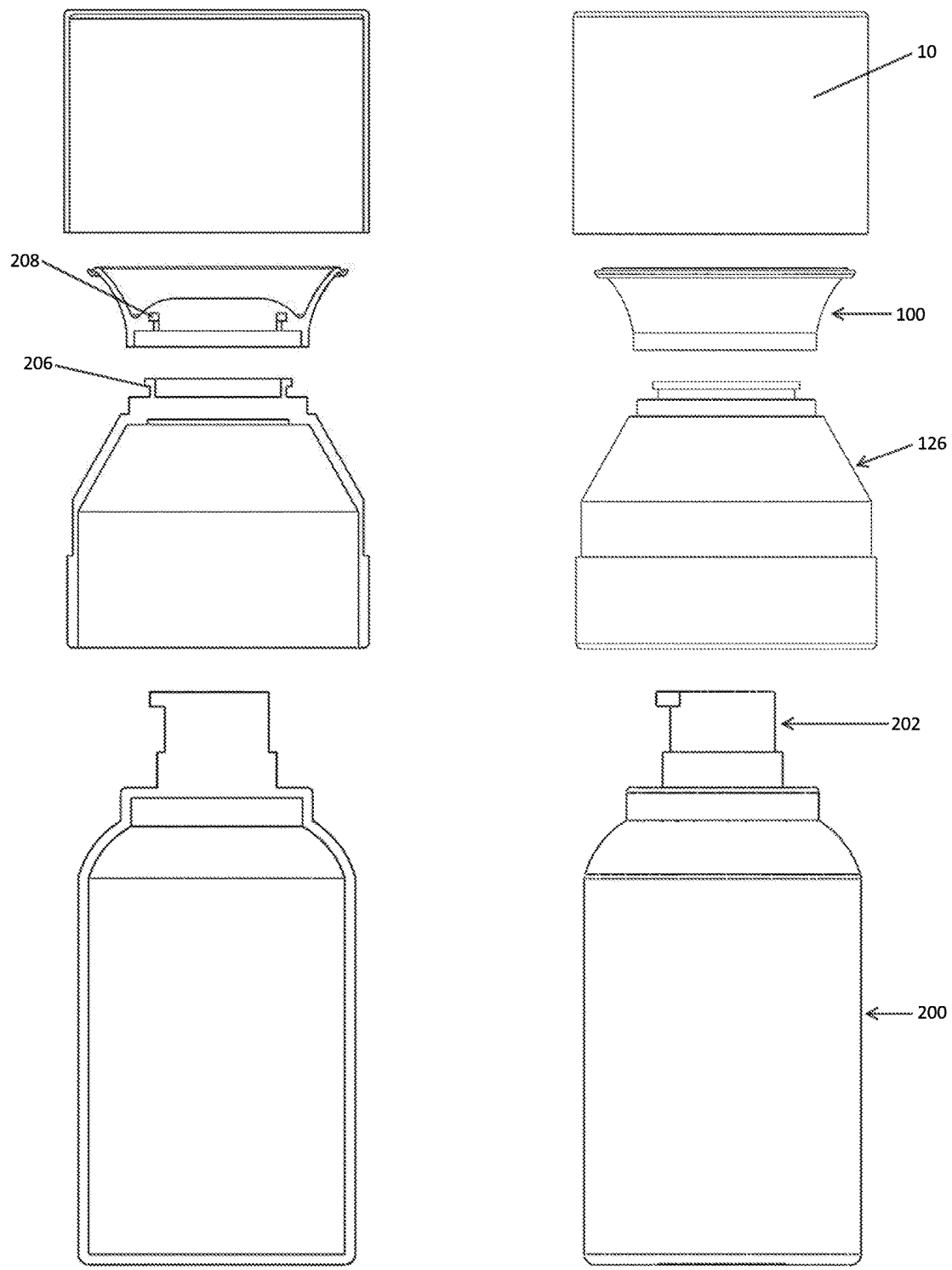
FIG. 1A depicts a side profile and a side-profile cutaway of an embodiment of the disclosure including a cap, an applying portion, a hold portion, and a composition holder with a pump head.

While embodiments of the disclosure are amenable to various modifications and alternative forms, specifics thereof are shown by way of example in the drawings and will be described in more detail below. It should be understood, however, that the intention is not to limit the disclosure to any one of the particular embodiments specifically addressed, or to the group of specifically addressed embodiments collectively. To the contrary, this disclosure covers all modifications, structural equivalents, functional equivalents, and alternatives falling within the spirit and scope of the disclosure. The drawings, which are not exhaustive of all embodiments and are not necessarily to scale, schematically depict illustrative embodiments and do not limit the scope of the claimed invention in any way.

DETAILED DESCRIPTION

As shown in FIG. 1A, some embodiments include a cap 10, an applying portion 100, a hold portion 126, and a composition holder 200 with a pump head 202. The cap 10 is configured to fit securely and removably over applying portion 100 and holder 126. In some embodiments, cap 10 and applying portion 100 are a single unit such that when 10 is inverted it reveals applying portion 100. In some such embodiments, cap 10 can be used as a holder and holder 126 is not included. Applying portion 100 is configured to securely attach to holder 126, as discussed in more detail below, with respect to FIGS. 3C, 3I, and 3J. Holder 126 is configured to fit securely and removably over pump head 202 and onto composition holder 200. This can be accomplished, for example, using a friction fit, including a twisting, snapping, or slighting type design. Applying portion 100 in this example includes an internal slot 208 that is configured to friction fit, either permanently or removably, with a lip 206 on holder 126. Some embodiments accomplish such a friction fit using one or more discrete tabs or lips and one or more corresponding internal or external slots. In other embodiments, holder 126 includes one or more internal slots and applying portion 100 includes one or more tabs or lips.

One way a user may use the embodiment depicted in FIG. 1A is to remove cap 10 from holder 126 remove holder 126 and applying portion 100 from composition holder 200 to reveal pump head 202. A user may then press down on pump head 202 to expel composition from composition holder 200 and into applying portion 100. The user can then apply the composition to one of the user's axilla regions by gripping the holder and stroking applying portion 100 around the region until a dose of the composition is applied.

Figure 1B:
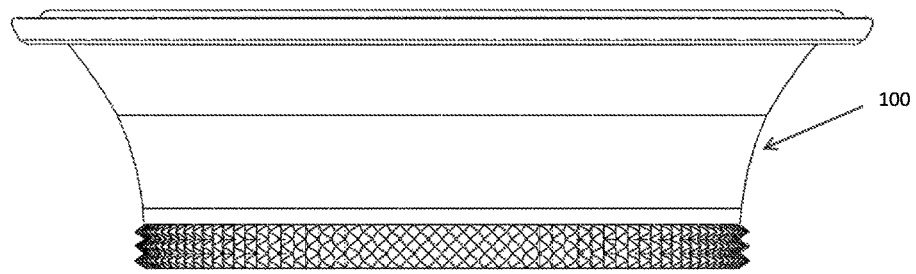
FIGS. 1B-1D depict an example embodiment of the disclosure including an applying portion.
Figure 1C:
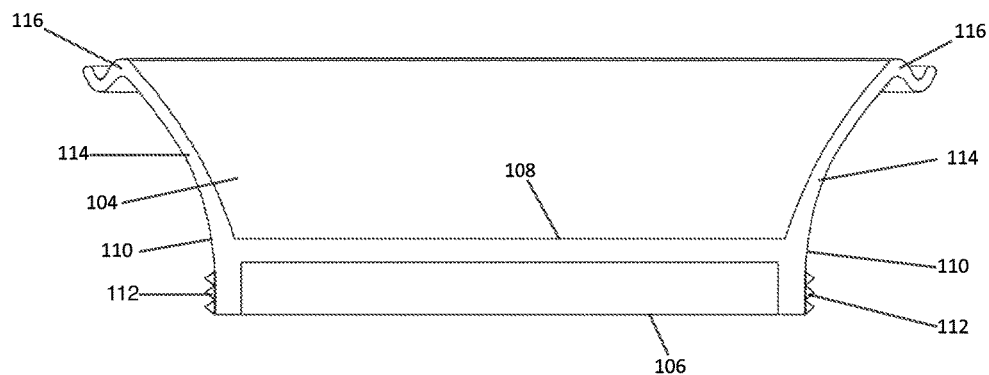
Figure 1D:
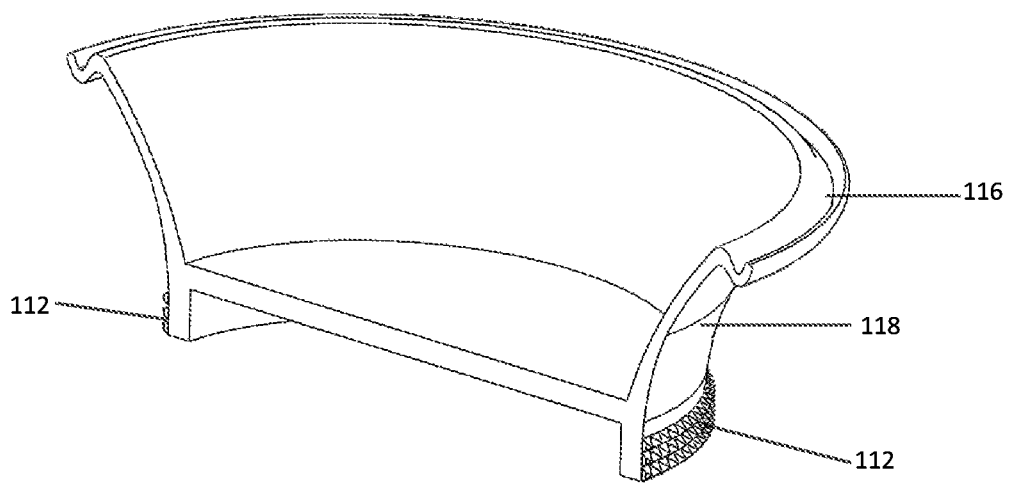

Referring to FIGS. 1B-D, an applying portion 100 generally includes a neck portion 102 and a cavity 104. In some embodiments, neck portion 102 and cavity 104 can be molded. In some embodiments, neck portion 102 and cavity 104 can be a unitary member. In other embodiments neck portion 102 and cavity 104 can be a molded unitary member. In other embodiments, neck portion 102 and cavity 104 can be separate components that can be removably coupled together. In other embodiments neck portion 102 and cavity 104 can be separate components permanently coupled together.

Neck portion 102 can include a lower-neck portion 106, a dividing portion 108, and a side wall 110. Lower-neck portion 106 and dividing portion 108 may constitute a unitary body or separate structures. Side wall 110 can include an outer surface 112 configured to enable a user to grip neck portion 102 for manipulation.

Cavity 104 can be coupled to dividing portion 108 of neck portion 102, which may or may not be fully or partially made of a porous surface or material. In some embodiments, cavity 104 can be constructed of a the same material as neck portion 102. In other embodiments, cavity 104 can be constructed of more rigid or more pliant material or materials than neck portion 102. Cavity 104 can have a side wall 114 extending longitudinally relative to dividing portion 108 to target-area contacting portion 116. Target-area contacting portion 116 can provide a seal between cavity 104 and skin which helps prevent composition from being applied to areas other than the target area. Side wall 114 can be constructed of a rigid or flexible material, such as synthetic or natural rubber or silicone.

As shown in FIG. 1D, some embodiments of an applying portion can include a side wall 114 having at least one controlled-adaptation zone 118, which may be fully or partially circumferential and which may be configured to provide flexibility or otherwise promote continuous contact between target-area contacting portion 116 and the target area by enabling side wall to adapt in shape in response to the contours of the target area. For example, controlled-adaptation zone 118 can be made of a pliant material that adapts in shape as applying neck portion 102 is stroked across a user's axilla.

In some embodiments, side wall 114 is releasably coupled to dividing portion 108. In other embodiments, side wall 114 is fixedly coupled to dividing portion 108. In other embodiments, side wall 114 is movably coupled to dividing portion 108. In some embodiments, side wall 114 and dividing portion 108 are molded or formed as a unitary member or structure, while in other embodiments, side wall 114 and dividing portion 108 are molded or formed as separate members or structures. In some embodiments, dividing portion 108 can serve as a top or bottom of cavity 104, while in other embodiments it can serve as a partial top or bottom of cavity 104. In other embodiments, dividing portion 108 does not serve as a top or bottom of cavity 104. In other embodiments, dividing portion 108 is removable and/or replaceable. Neck portion 102 and a dividing portion 108 may or may not be separate and independent structures. Further, cavity 104 may be used or stored in a position that is fully or partially rotated or inverted when compared to the embodiments shown in FIGS. 1B-D. For example, in some embodiments cavity 104 can be disposed vertically beneath neck portion 102 and dividing portion 108, such that applying portion 100 is inverted by a user to prepare for use.

As shown, for example, in FIGS. 1C and 1D, in some embodiments, dividing portion 108 can be fully, substantially, or partially planar. As shown, for example, in FIGS. 4B-E, in other embodiments, dividing portion 108 can be fully, substantially, or partially convex or curved upwards towards an interior of the applying portion porous surface, and/or downwards away from the interior of the applying portion porous surface. In some embodiments, dividing portion 108 comprises a porous or other material or padding and/or air that provides enhanced adaptability when pressed against a user's body and/or acts to press or spread a composition contained within cavity 104 on a user's body during use. In some such embodiments, dividing portion 108 is adaptable in response to pressure such that it changes in shape in response to pressure, as when it is pressed against a user's body when a composition is being applied, and substantially returns to its original shape if the pressure is released, as when a dose of the composition has just been applied. In some embodiments, dividing portion 108 can also be fully, partially, or substantially permeable, such as a porous, sponge, matrix, membrane, thread, capillary, and/or other material. In some embodiments, dividing portion 108 can provide for fluid communication, and/or mixing with one or more solutes, solvents, including gases. In other embodiments, dividing portion 108 does not provide for fluid communication, but acts as a barrier to fluid transfer from cavity 104—e.g., as a barrier to fluid transfer from cavity 104 to neck portion 102.

Referring to FIGS. 2A-D, in some embodiments, at least a portion of side wall 114 can be fully, partially, or substantially conical, pyramidal, frustoconical, or otherwise have one or more frustums and/or outward flares from dividing portion 108 and/or neck portion 102. In some embodiments, side wall 114 can flare outwardly from dividing portion 108 along a fully, partially, or substantially linear and/or non-linear curve, such as a fully, partially, or substantially hyperboloid, paraboloid, ellipsoid, and/or elliptic paraboloid curve.

Figure 2A:
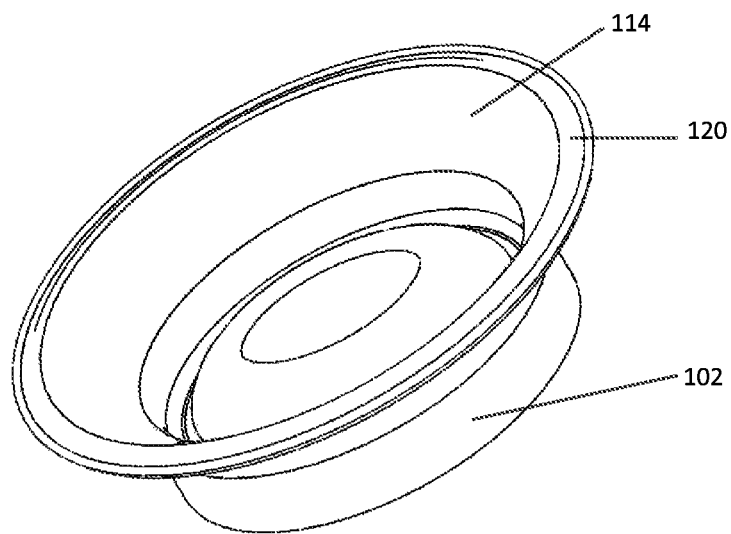
FIGS. 2A-2G depict further example embodiments of the disclosure including an applying portion.
Figure 2B:
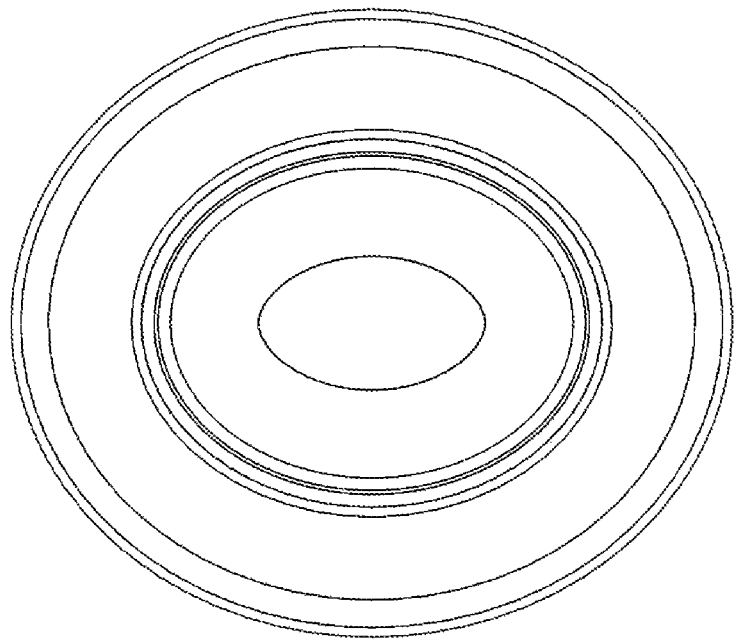
Figure 2C:
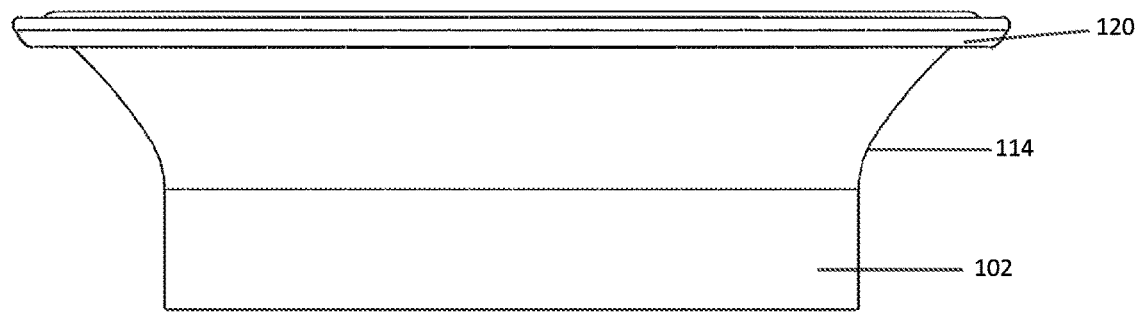
Figure 2D:
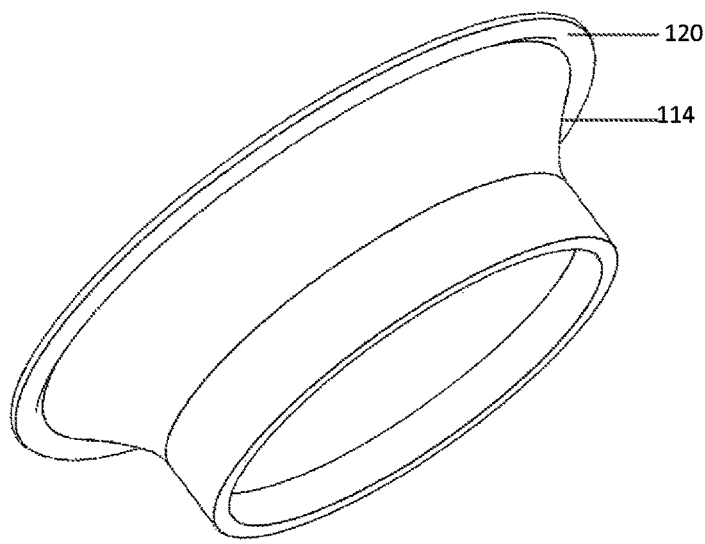

As shown in FIG. 2A, some embodiments include a target-area contacting portion 116 with an extension 120 from side wall 114, thereby providing additional surface area which may contact the target area of the user. For example, in one embodiment, side wall 114 can be formed from a relatively flexible membrane which allows extension 120 to flex, thereby acting like a runner when spreading medicament, such as a medicated liquid, foam, cream, or gel, across the treatment surface.

In some embodiments, target-area contacting portion 116 can be fully, partially, or substantially elliptical in shape in a manner disposed to conform to an axilla region of the user. In other embodiments, target-area contacting portion 116 can have or resemble other shapes and/or textures, such as an inwardly or outwardly ridged surface, an inwardly or outwardly indented surface, a finned surface, a bristled surface, a node surface, a surface, a dome surface, a comb surface, a spherical surface, a crescent surface, a notched surface, or a generally rounded configuration. In some embodiments, target-area contacting portion 116 includes a combination of such shapes. The specific shape the target-area contacting portion 116 and/or extension 120 can be adapted to conform to any specific prescribed target area or to a group of optional target areas.

Figure 2E:
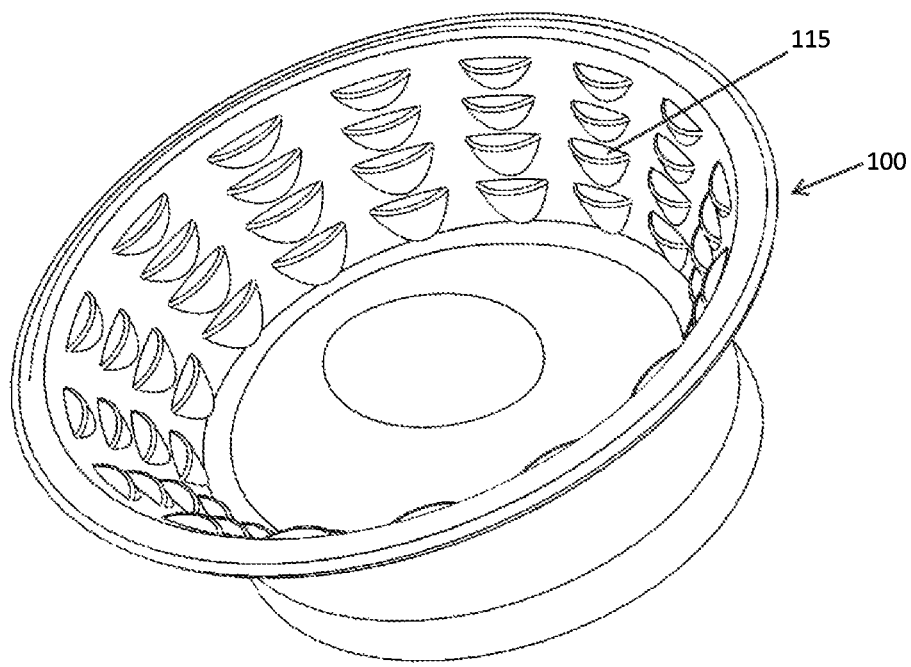
Figure 2F:
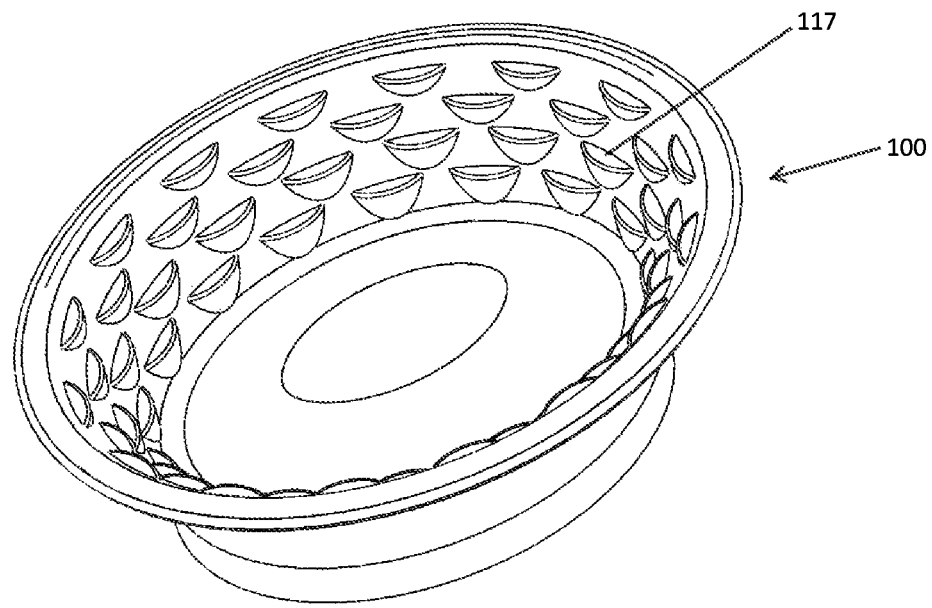
Figure 2G:
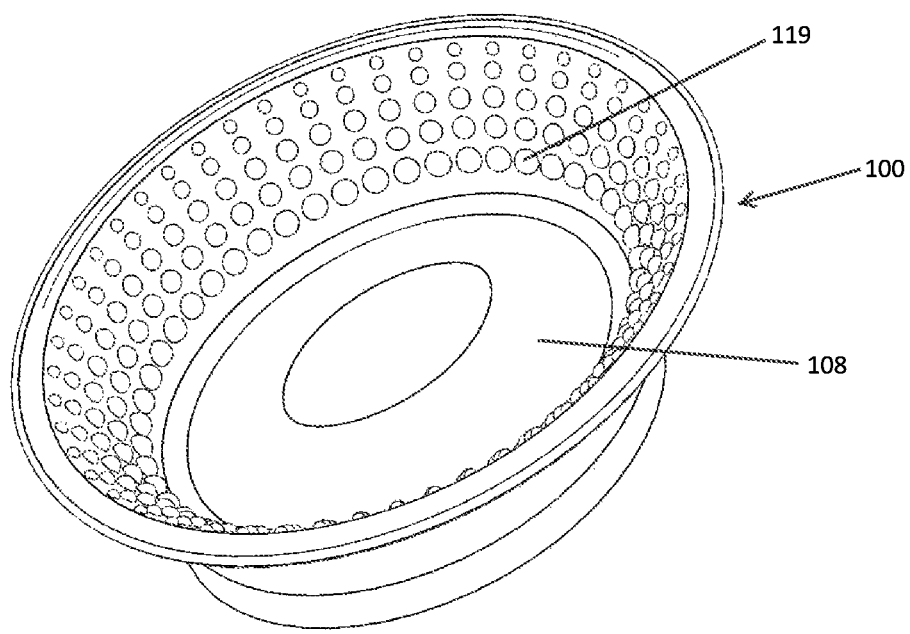

In some embodiments, applying portion 100 comprises a side wall with areas of varying thickness, such as protrusions or indentations. As shown in FIGS. 2E-G, in some embodiments, applying portion 100 has a side wall that includes a pattern of protrusions from the side wall, such as linearly stacked cusps 115, staggered cusps 117, or domes 119. Cusps 115, staggered cusps 117, and domes 119 may be uniformly or non-uniformly sized and may provide texture that assists with the application of a composition. For example, FIG. 2G shows linearly arranged domes 119 of decreasing circumference as the lateral distance from dividing portion 108 increases. Like cusps 115 and staggered cusps 117, domes 119 may be stacked linearly, as shown, or staggered, either regularly or irregularly. In other embodiments, a side wall includes one or more other shapes and/or textures, such as an inwardly or outwardly ridged surface, an inwardly or outwardly indented surface, a finned surface, a bristled surface, a node surface, a surface, a comb surface, a spherical surface, a crescent surface, a notched surface, or a generally rounded configuration. In some embodiments, a side wall includes a combination of such shapes and/or textures. In some embodiments, a side wall includes shapes and/or textures on an external surface facing away from cavity 104. Some embodiments include shapes and/or textures designed to achieve one or more controlled-confirmation zones for optimal conformability, collapsibility, and/or expandability. In some embodiments, protrusions and/or indentations on a side wall of the applying portion 100 are configured to provide an enhanced friction fit for an absorptive material placed within cavity 104.

Figure 3J:
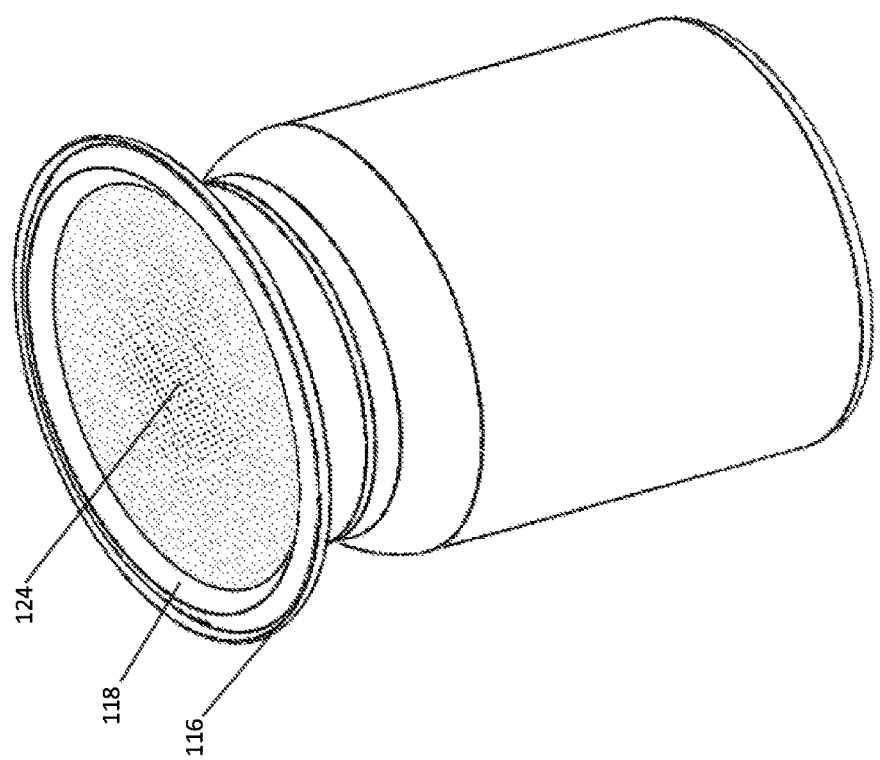

Referring to FIGS. 3A-J, in some embodiments, a controlled-adaptation zone 118 of side wall 114 can be configured to collapse longitudinally. For example, when pressure is applied to target-area contacting portion 116, applying portion 100 side wall 114 is at least partially collapsed, as shown by comparing FIGS. 3A and 3B with FIGS. 3E and 3F, comparing FIG. 3D with FIG. 3H, and comparing FIG. 3I with FIG. 3J. In some embodiments, controlled-adaptation zone 118 is comprised of one or more folds 122 molded into the side wall. In some embodiments, folds 122 may be fully, partially, or substantially circumferential.

As further depicted in FIGS. 3C-J, cavity 104 can include an absorptive material 124. Absorptive material 124 can be configured to absorb, temporarily retain, and/or dispense or release a dose of medicinal liquid composition, for example, thereby reducing the likelihood and/or amount of spillage. Absorptive material 124 can be a sponge, foam, matrix, or other porous or partially porous configuration or composition capable of at least temporarily absorbing a composition in one or more volumes, powders, or doses. As shown in FIGS. 3B, 3F, 3H, and 3J, side wall 114 may be at least partially collapsed to expose some or more absorptive material 124 for contact with the target area. Additionally, some embodiments absorptive material 124 can be omitted in favor of a lattice arrangement which may or may not be absorptive, such as a lattice-arrangement pad, which is fully or partially absorptive. In some embodiments a lattice-arrangement pad holds the composition until it is applied to a target area and then releases all or a portion of it at the target area. In some embodiments, absorptive material 124 can be square, oval, elliptical, circular, polygonal, inwardly or outwardly ridged, inwardly or outwardly indented, finned, bristled, noded, follicular, spherical, cylindrical, crescent, discoid, semi-discoid, crescent, or generally rounded in configuration.

Figure 3I:
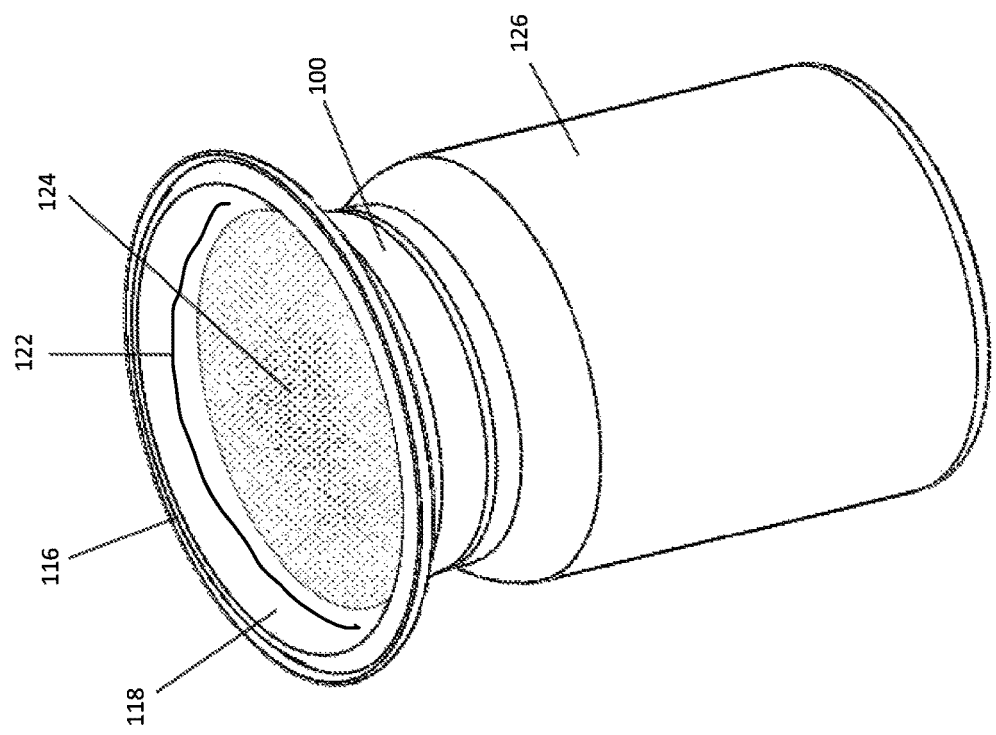
Figure 4A:
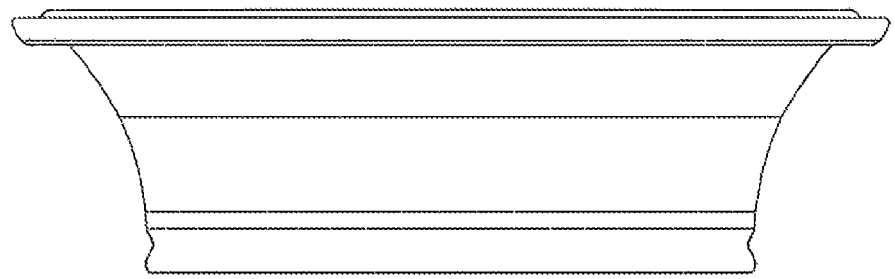
FIGS. 4A-4E depict a further embodiment of the disclosure including an applying portion.
Figure 4B:
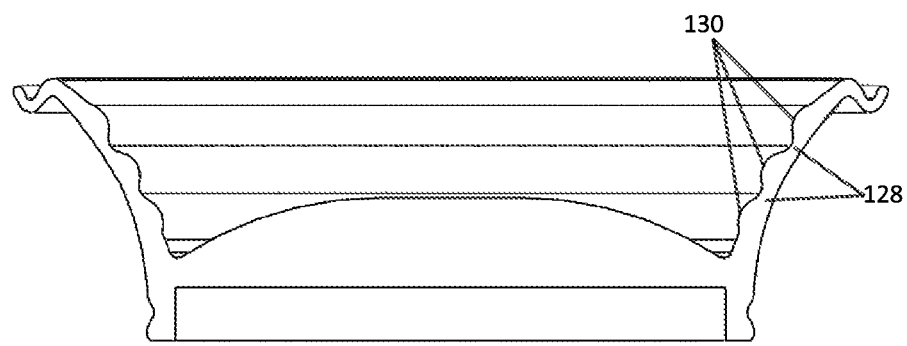
Figure 4C:
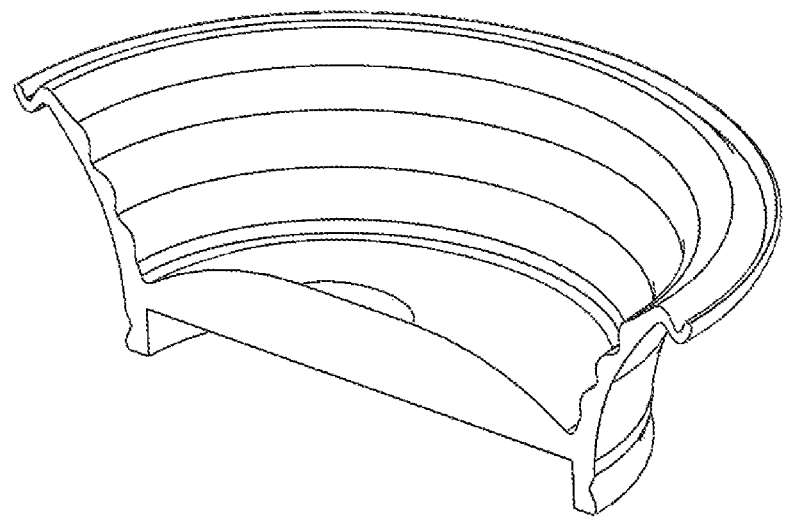
Figure 4D:
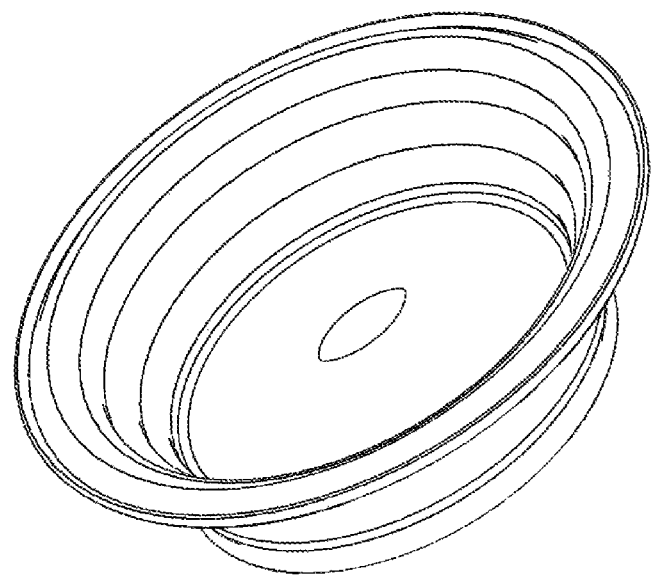
Figure 4E:
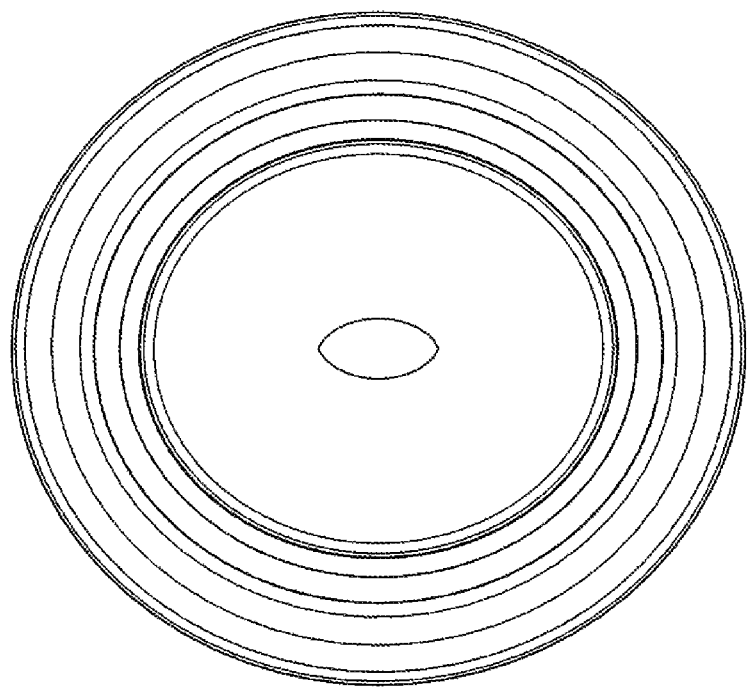
Figure 5A:
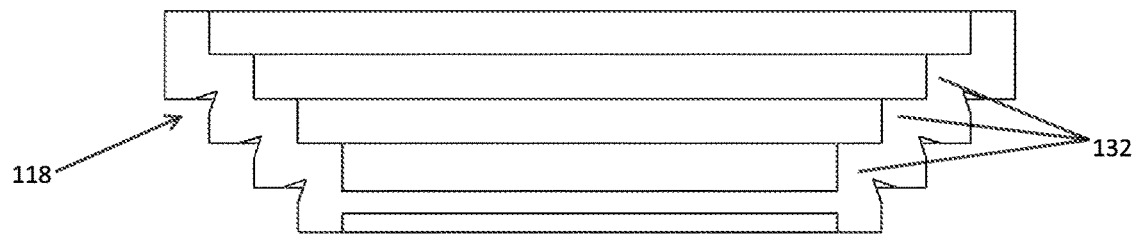
FIGS. 5A-5D depict a further embodiment of the disclosure including an applying portion.
Figure 5B:
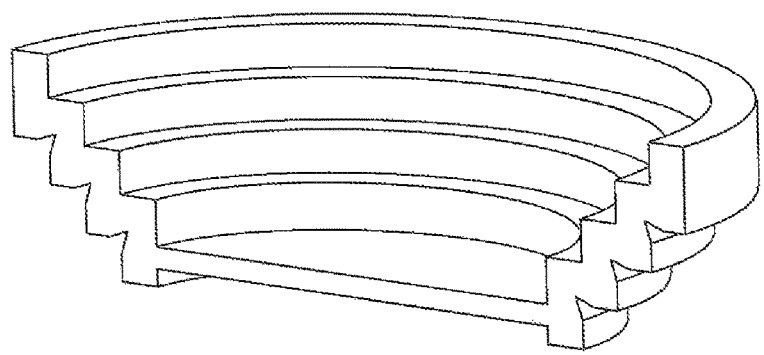
Figure 5C:
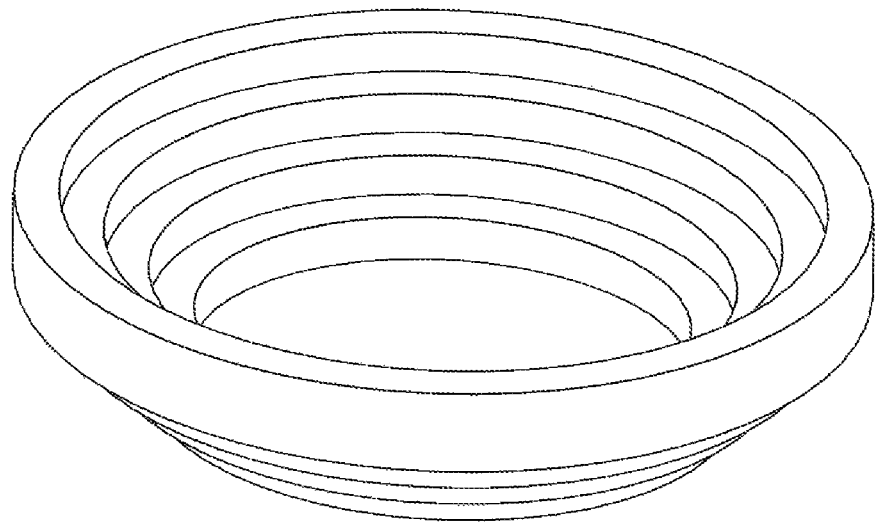
Figure 5D:
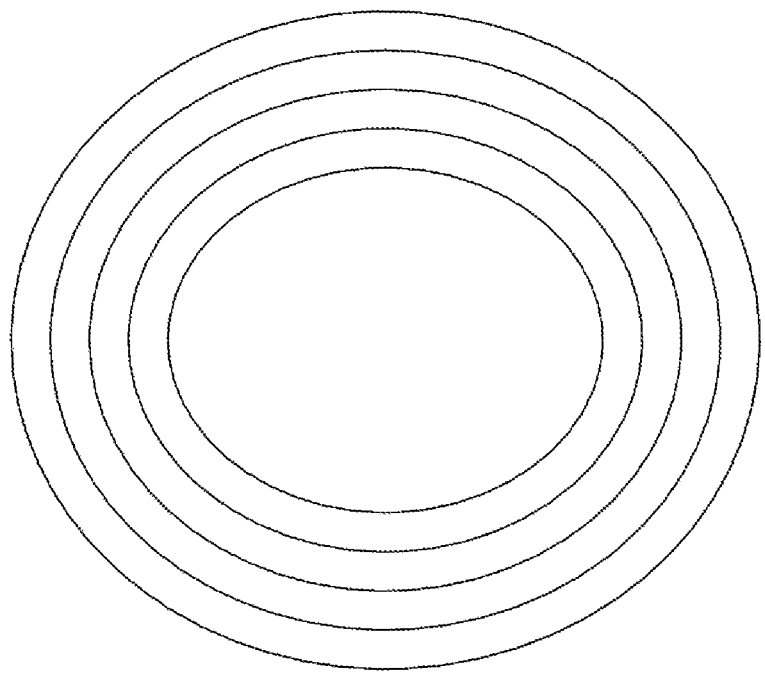

As shown in FIGS. 3C, 3I, and 3J, for example, in some embodiments, applying portion 100 can be coupled to a holder 126. In some embodiments, holder 126 can be a fully or partially hollow configuration which fits snugly onto or around a permanent or replaceable medicinal container or cartridge. In some embodiments, lower-neck portion 106 can be adapted to be, or couple to, a medicinal liquid composition container. In some embodiments, side wall 114 may be glued or otherwise fixed, attached, coupled, and/or bonded to holder 126. In some embodiments, side wall 114 is releasably attached to holder 126. For example, lower-neck portion 106 can threadedly couple to holder 126, or holder 126 can be a hollow plastic component which can fit snugly onto the medicinal container. In other embodiments, one or more clamps or other engagement mechanisms can couple side wall 114 to holder 126.

In some embodiments, applying portion 100 can create a non-permeable, one-way, and/or fluid-tight seal, thereby serving as a top for holder 126 that can prevent its contents from leaking or spilling. In some embodiments, applying portion 100 and/or dividing portion 108 provide(s) a one-way, reversible seal that allows fluid compositions to pass from composition holder 200 and into cavity 104 or an absorptive material 124 contained in or by cavity 104 without removing holder 126 from composition holder 200. In some such embodiments, holder 126 and composition holder 200 are combined into a single unit.

In some embodiments, the dividing member has an absorptive pad coupled to one side. In some such embodiments, the applying portion includes on one side of a dividing member two threaded neck portions, a target-area contacting portion, and absorptive pad, and a cavity. In such embodiments, one threaded neck portion can be screwed onto a composition holder to secure the absorptive pad in a sealed position facing into the composition holder. When a user wants to use such an embodiment to apply a composition held in the holder, the user may unscrew the first threaded-neck portion, invert the applying portion to expose the absorptive pad, screw the second threaded-neck portion onto the composition holder, apply the composition, and, when finished, invert the applying portion again for storage. In some such embodiments, at least one of two neck members is adapted to also serve as the target-area contacting portion.

Referring to FIGS. 4A-E, in one embodiment, controlled-adaptation zone 118 can include one or more side wall areas 128 having controlled-adaptation features, such as a reduced wall thickness interspaced between one or more portions of a greater wall thickness 130. In some embodiments, a controlled-adaptation feature constitutes two or more ribs of a greater thickness 130 than adjacent regions of a side wall and can provide structural integrity to side wall 114, while one or more other side wall areas have a reduced wall thickness and can better yield to stress applied to side wall 114 in the longitudinal direction.

In some embodiments, side wall 114 can include at least one, and preferably two or more, spaced controlled-adaptation features on its inside and/or outside surface, such as grooves, ridges, or folds, that traverse one or more portions of side wall 114 between a dividing portion 108 and a target-area contacting portion 116. In some embodiments, the controlled-adaptation features traverse the circumferential or longitudinal length of side wall 114. In some embodiments, the controlled-adaptation features traverse only a portion of the circumferential or longitudinal length of side wall 114. In some embodiments, the controlled-adaptation features traverse substantially horizontal, diagonal, latitudinal, or circumferentially spaced portions of side wall 114. In other embodiments, the controlled-adaptation features traverse substantially vertical, diagonal, or longitudinally spaced portions of side wall 114. In some embodiments, the controlled-adaptation features traverse waved, sinusoidal, or zigzag portions of side wall 114. In still other embodiments, controlled-adaptation features traverse a combination of the above exemplary, but nonexclusive, list of options. In this way, side wall 114 can be adapted to longitudinally adapt such that target-area contacting portion 116 moves longitudinally inward to expose the top and/or sides of an absorptive pad coupled to a divider portion in response to an applied force, such as when pressed onto the skin of a user. In some embodiments, the applied force may be electromagnetic, such as through the application of current through spaced conductive wires. In other embodiments, side wall 114 can be made of a material that softens when exposed to body heat, such that it is stiffer when not in contact with human skin, and more pliant when it is in contact with human skin. In some embodiments, a ribbed side wall allows for longitudinal adaptation and ensures that gravity causes a liquid composition to flow back to absorptive pad or sponge, thus minimizing the chances of spillage. One or more groups, ribs, or folds can also serve to temper the distribution of compound at the target area.

Referring to FIGS. 5A-D, in one embodiment, controlled-adaptation zone 118 can include one or more steps 132 on side wall 114. In some embodiments, steps 132 are molded onto and/or within side wall 114. In other embodiments, steps 132 are cut or etched into side wall 114. Steps 132 can be designed to collapse, thereby facilitating a telescoping effect to reduce the interior volume of cavity 104.

Figure 6A:
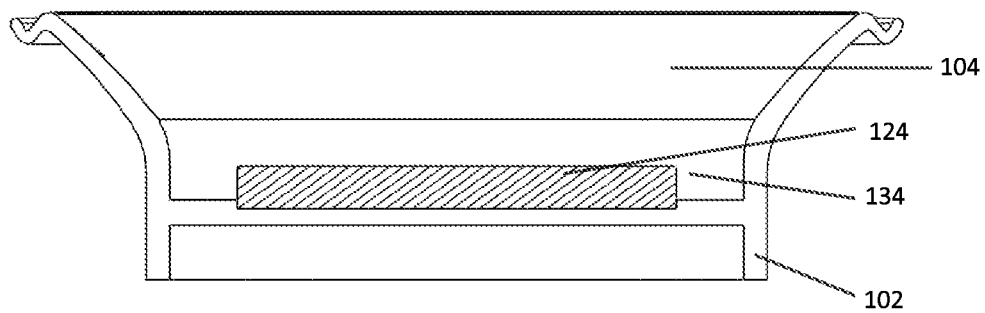
FIGS. 6A-6B depict a further embodiment of the disclosure including an applying portion.
Figure 6B:
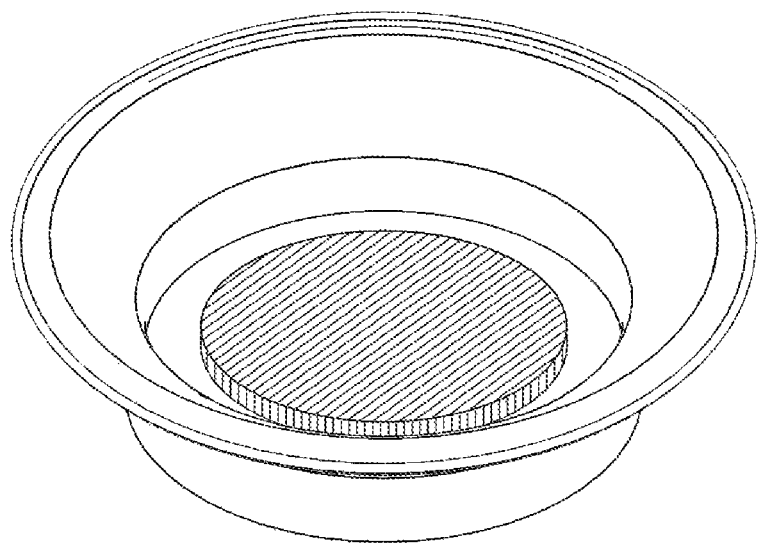
Figure 7A:
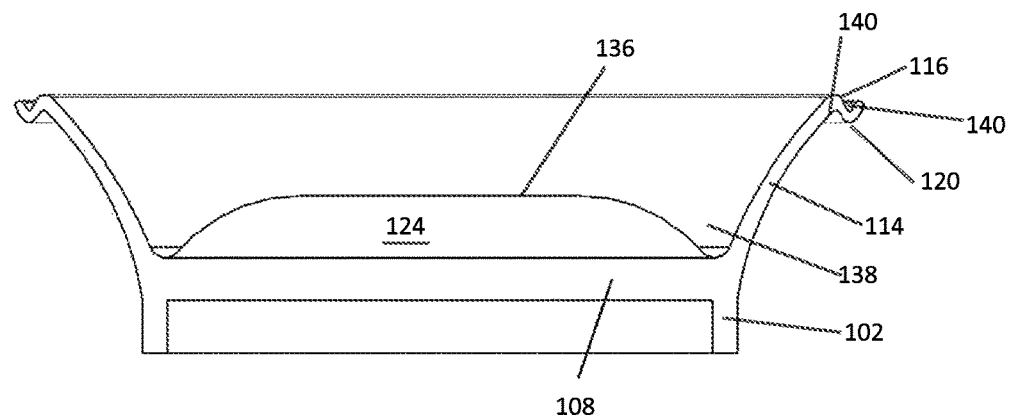
FIGS. 7A-7B depict a further embodiment of the disclosure including an applying portion.
Figure 7B:
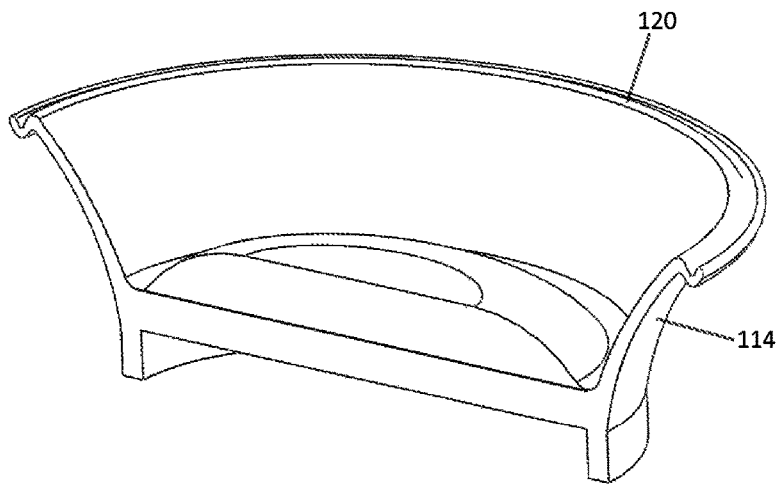
Figure 8A:
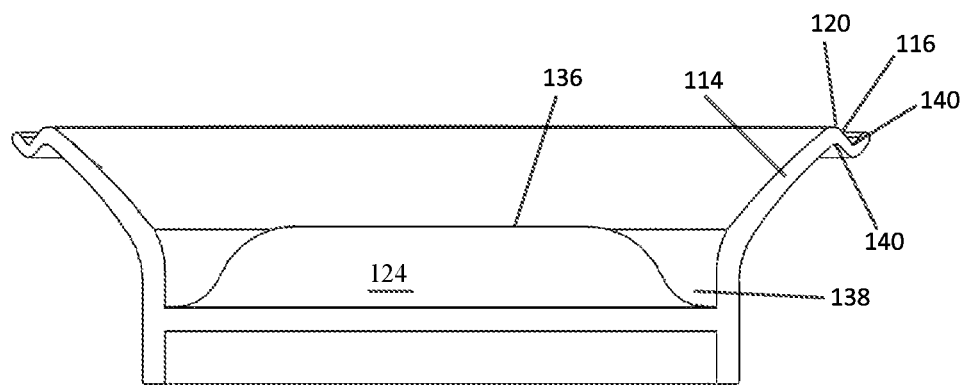
FIGS. 8A-8B depict a further embodiment of the disclosure including an applying portion.
Figure 8B:
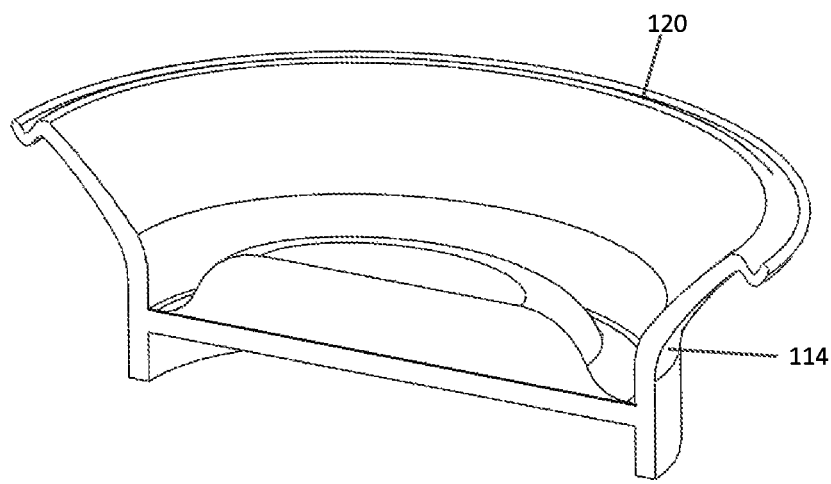

Referring to FIG. 6A-B, in one embodiment, cavity 104, or dividing portion 108, can include a recess 134 for receiving absorptive material 124 and configured to hold a dose or amount of a composition, such as a medicinal liquid. For example, in some embodiments, absorptive material 124 is shaped to correspond or adapt to the shape of recess 134. In such embodiments, absorptive material 124 can be retained in recess 134 by friction or interference fit. In other embodiments, an adhesive or mechanical apparatus and/or configuration can be used to secure absorptive material 124 within recess 134 permanently or removably. In other embodiments, absorptive material 124 can be releasably mounted proximal to neck portion 102 in other configurations.

Referring to FIGS. 7A-B and 8A-B, in some embodiments, absorptive material 124 can have a rounded edge 136 that conforms and/or adapts to the surface to which a composition, such as a medicinal liquid, is to be applied. In some embodiments, the shape of absorptive material 124 can create an annular, semi-annular, or periodically spaced groove 138 between absorptive material 124 and side wall 114. In some embodiments, target-area contacting portion 116 can include an extension 120 from the side wall 114 that includes one or more folds 140. In some embodiments, the extension is a lateral extension. In other embodiments, the extension extends laterally inward toward the longitudinal axis of the applying portion. In still other embodiments, the extension extends laterally outward from the longitudinal axis of the applying portion. In some embodiments, one or more folds 140 may be fully, partially, or substantially circumferential. The one or more circumferential folds 140 can, for example, increase the flexibility and/or collapsibility of target-area contacting portion 116, thereby enabling extension 120 to flex.

In some embodiments, a dose or amount of medicinal liquid can be applied to absorptive material 124, and absorptive material 124 can be placed into cavity 104. For example, absorptive material 124 can be provided in a predetermined dosed configuration separately from cavity 104. In some embodiments, cavity 104 is reusable, whereas absorptive material 124 is individually packaged for one-time use. In other embodiments, applying portion 100 and absorptive material 124 are individually packaged for one-time use. In other embodiments, dividing portion 108 of can be configured to selectively enable a dose or amount of a composition, such as a medicinal liquid composition, to be dispensed directly from within holder 126, or composition holder 200, to absorptive material 124, without the need to remove absorptive material 124 from cavity 104. In such an embodiment, neck portion 102 is configured to fully, partially, or substantially sealingly engage holder 126. Dividing portion 108 of neck portion 102 can include a one or more apertures terminating at recess 134, thereby enabling medicinal liquid composition to flow through apertures onto absorptive material 124.

In some embodiments, after a composition has been applied, an undelivered amount of composition may remain associated with or within holder 126, composition holder 200, and/or applying portion 100. Applying portion 100 can be removed from holder 126, and absorptive material 124 can be discarded or washed, along with cavity 104. Applying portion 100 can be removed from holder 126, and absorptive material 124 can be discarded or washed, along with cavity 104.

Applying portion 100 and the absorptive material 124 may be constructed of any suitable material, such as silicone, silicone rubber, or other medical- or nonmedical-grade material. In one embodiment, applying portion 100 is constructed of a material certified to meet FDA CFR 177.2600, EC 1935/2004 and/or EU 10/2011 requirements. Applying portion 100 may comprise Grade 2600 FDA compliant silicone, HAPLEX an elastomeric polymer being extremely durable and impact resistant, HAPSIL a high tear strength tin catalyzed RTV-2 silicone rubber, STERALLOY an FDA grade polymer, S-RIM a production grade casting resin, TUFFALLOY a rigid liquid molding compound having thermoplastic properties, ULTRACAST a low shrink low viscosity material, and/or any combinations thereof.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. An applicator for administering a composition to a target area comprising:
   an applying portion comprising a cavity with at least one open portion, the cavity comprising a porous volume and defined, at least in part, by at least one side wall, the side wall comprising at least one controlled-adaptation zone;
   a dividing portion adjacent to, and opposite the at least one open portion of, the cavity; and
   a target-area contacting portion adapted to create a seal between the at least one open portion of the cavity and the target area to which the composition is being applied;
   wherein the controlled-adaptation zone is coupled to the target-area contacting portion and adapted to flexibly promote continuous contact between the target-area contacting portion and the target area.

2. The applicator of claim 1, wherein the side wall comprises areas of varying thickness.

3. The applicator of claim 2, wherein the areas of varying thickness are protrusions, indentations, or both protrusions and indentations.

4. The applicator of claim 1, wherein the porous volume comprises a matrix.

5. The applicator of claim 1, wherein the target-area contacting portion comprises a fold, a groove, or a rib.

6. The applicator of claim 1, wherein the dividing portion is at least partially convex in shape.

7. The applicator of claim 1, wherein the porous volume comprises an absorptive material.

8. The applicator of claim 1, wherein the dividing portion comprises a region configured to receive an absorptive material.

9. The applicator of claim 1, wherein the dividing portion comprises an absorptive material.

10. The applicator of claim 1, wherein the dividing portion allows a composition to move through it to the cavity.

11. The applicator of claim 1, wherein:
    the porous volume is disposed within the cavity adjacent to the dividing portion; and
    the at least one controlled-adaptation zone is configured to flexibly adapt such that at least a portion of the porous volume moves closer to the target area in response to a force.

12. The applicator of claim 1, wherein:
    the porous volume is disposed within the cavity adjacent, to the dividing portion; and
    the target-area contacting portion comprises a portion that extends beyond the cavity side wall and is configured to adapt to the target area in response to a force.

13. The applicator of claim 1, wherein the applicator is configured to releasably and sealingly couple to a composition holder that is at least partially hollowed, that is configured to hold a composition, and which comprises a side wall, a bottom, and a gripping surface.

14. The applicator of claim 1, further comprising a holder configured to releasably attach to the applying portion and a composition holder.

15. The applicator of claim 14, wherein the applying portion and the composition holder are configured to releasably and sealingly couple to one another.

16. A system for administering a composition to a target area comprising the applicator of any of claims 1-9, 10-13, 14 and 15.

* * * * *